US008517027B2

(12) United States Patent
Haig

(10) Patent No.: US 8,517,027 B2
(45) Date of Patent: Aug. 27, 2013

(54) REVERSIBLE VESSEL SEAL

(75) Inventor: Nancy Haig, East Bethel, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 225 days.

(21) Appl. No.: 10/934,837

(22) Filed: Sep. 3, 2004

(65) Prior Publication Data

US 2006/0052820 A1 Mar. 9, 2006

(51) Int. Cl.
*A61F 6/06* (2006.01)
*A61M 29/00* (2006.01)
*A61F 2/06* (2013.01)

(52) U.S. Cl.
USPC .................... 128/831; 606/192; 623/1.11

(58) Field of Classification Search
USPC .................. 128/843, 831, 833, 887; 623/1.1, 623/1.15, 1.2, 1.22, 1.38, 1.49, 1.5, 1.51, 623/1.16, 1.18, 1.11, 1.12, 1.24; 606/200, 606/151, 213, 191, 192; 424/430, 436, 423; 600/200

See application file for complete search history.

(56) References Cited

U.S. PATENT DOCUMENTS

| 5,474,089 | A |   | 12/1995 | Waynant |            |
|-----------|---|---|---------|---------|------------|
| 5,549,663 | A | * | 8/1996  | Cottone, Jr. | 623/1.22 |
| 5,665,115 | A | * | 9/1997  | Cragg   | 623/1.13   |
| 5,681,274 | A |   | 10/1997 | Perkins et al. |     |
| 5,824,054 | A | * | 10/1998 | Khosravi et al. | 623/1.44 |
| 6,193,748 | B1 | * | 2/2001 | Thompson et al. | 623/1.3 |
| 6,358,556 | B1 |   | 3/2002 | Ding et al. |       |
| 6,387,122 | B1 | * | 5/2002 | Cragg | 623/1.16 |
| 6,416,540 | B1 | * | 7/2002 | Mathur | 623/1.15 |
| 6,432,116 | B1 | * | 8/2002 | Callister et al. | 606/157 |
| 2002/0029051 | A1 | * | 3/2002 | Callister et al. | 606/157 |
| 2003/0229366 | A1 |   | 12/2003 | Reggie et al. |  |
| 2004/0098030 | A1 |   | 5/2004 | Makower et al. |   |
| 2005/0055039 | A1 | * | 3/2005 | Burnett et al. | 606/151 |
| 2006/0009798 | A1 | * | 1/2006 | Callister et al. | 606/200 |
| 2006/0149351 | A1 | * | 7/2006 | Smirthwaite et al. | 623/1.13 |

FOREIGN PATENT DOCUMENTS

EP 0749729 12/1996

* cited by examiner

*Primary Examiner* — Patricia Bianco
*Assistant Examiner* — Tarla Patel
(74) *Attorney, Agent, or Firm* — Mayer & Williams PC; David B. Bonham

(57) ABSTRACT

A vessel seal for reversibly sealing a body lumen comprises a support structure moveable between an insertion and deployed configuration, wherein a diameter of the support structure in the deployed configuration is greater than in the insertion configuration, and is substantially corresponding to an inner diameter of a lumen. A compressible vessel seal is coupled to the support structure so that, when in the deployed configuration, the vessel seal expands to occlude the lumen. A method of controlling flow through a body lumen, comprises the steps of inserting into a lumen a vessel seal assembly including a support structure and a compressible vessel seal coupled thereto and moving the support structure to a deployed configuration in which the vessel seal expands to occlude the lumen, wherein a diameter of a support structure in the deployed configuration is greater than in the insertion configuration and substantially corresponds to an inner diameter of the lumen.

15 Claims, 3 Drawing Sheets

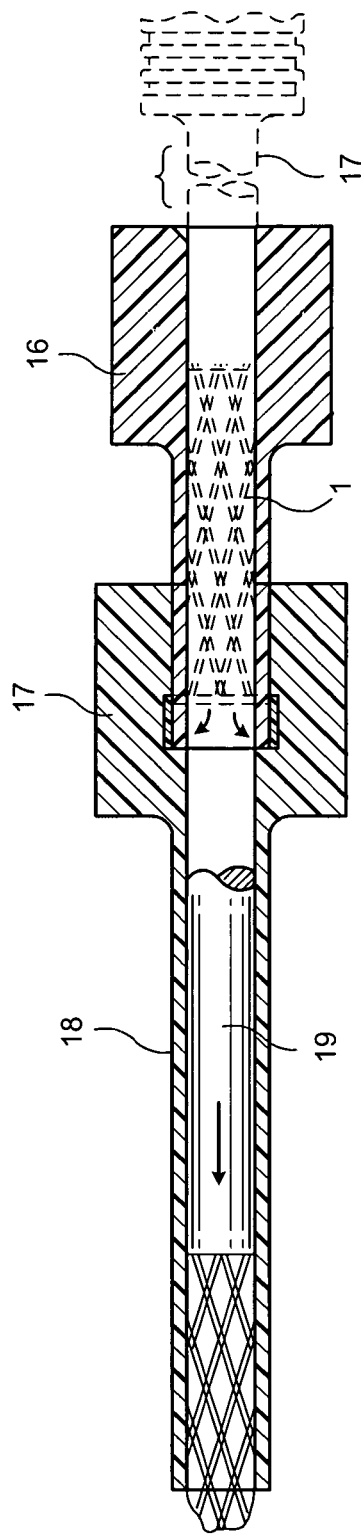
F I G. 3
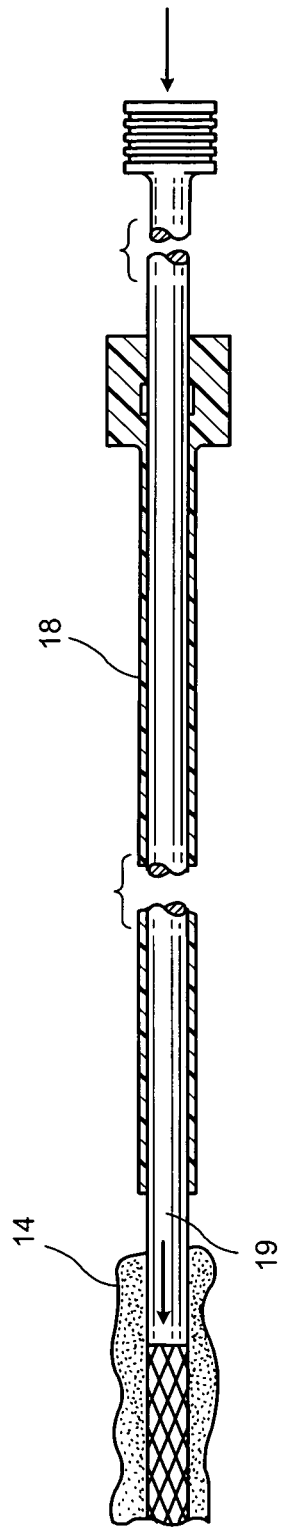
F I G. 4

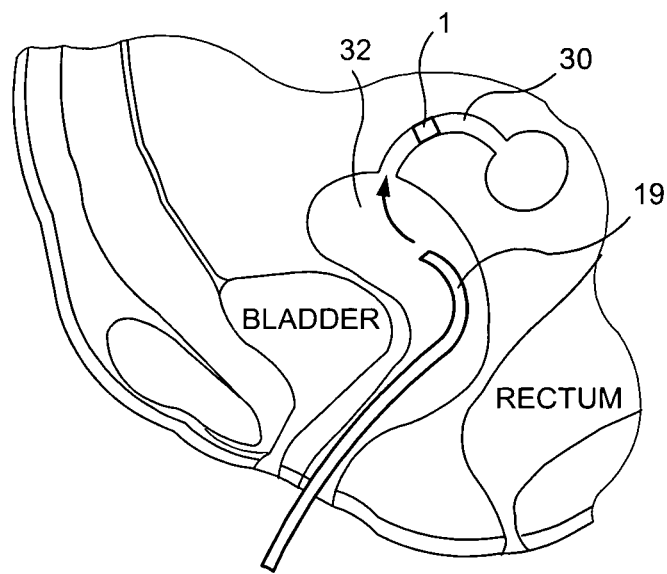
F I G. 5
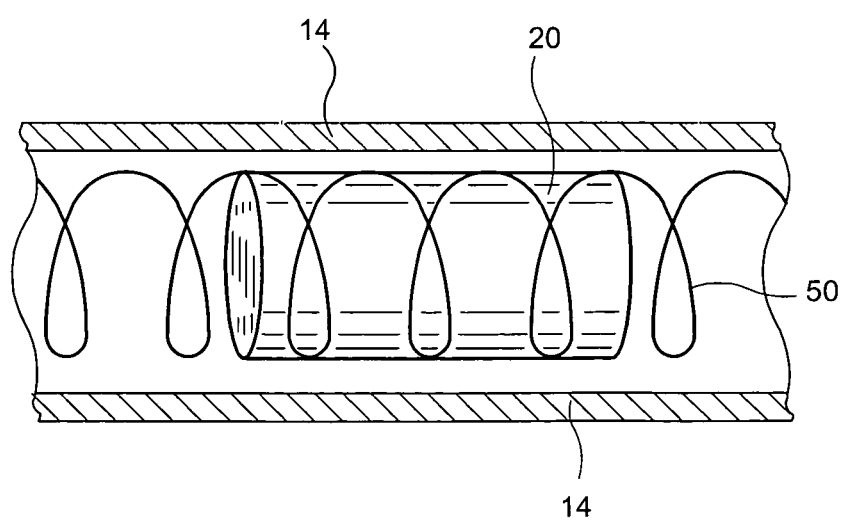
F I G. 6

REVERSIBLE VESSEL SEAL

FIELD OF THE INVENTION

The present invention generally relates to devices and methods for creating reversible seals within body lumens.

BACKGROUND

Conventional medical procedures which require that a patient's vessel be indefinitely sealed have often related to long-term contraception. For females, conventional contraceptive procedures have involved the implantation of intrauterine devices or surgical measures to cut or block the fallopian tubes. These procedures have been reversed by removing blocking devices (e.g., clips, rings, etc.) or by using microsurgery to repair the damage done by cautery or cutting in order to reconnect previously severed vessels. For males, a vasectomy procedure which cuts the vasa deferntia, has generally been utilized as a primary conventional method of contraception. Vasectomies have been reversed by reconnecting the vasa deferntia via microsurgical techniques.

Although conventional contraception procedures have been effective in providing long-term contraception, these procedures may reduce or completely stop blood flow to critical reproductive organs which may in turn significantly reduce the potential to restore the organs' function if this is desired at a later time. In addition, microsurgery required to reverse these procedures has often proven difficult.

SUMMARY OF THE INVENTION

The present invention is directed to a vessel seal for reversibly sealing a body lumen comprising a support structure moveable between an insertion configuration and a deployed configuration, wherein a diameter of the support structure is greater in the deployed configuration than in the insertion configuration, a diameter of the support structure in the deployed configuration substantially corresponding to an inner diameter of a target portion of the body lumen at which the support structure is to be deployed and a compressible vessel seal coupled to the support structure so that, when the support structure is in the deployed configuration, the vessel seal expands within a central lumen of the support structure to occlude the body lumen. In certain embodiments, the compressible vessel seal comprises a solid biocompatible, non-biodegradable material.

The present invention is further directed to a method of controlling flow through a body lumen, comprising the steps of inserting into a target portion of a body lumen a vessel seal assembly in an insertion configuration, the vessel seal assembly including a support structure and a compressible vessel seal coupled thereto and moving the support structure to a deployed configuration in which the vessel seal expands within a central lumen of the support structure to occlude the body lumen, wherein a diameter of a support structure is greater in the deployed configuration than in the insertion configuration and a diameter of the support structure in the deployed configuration substantially corresponds to an inner diameter of the target portion of the body lumen.

BRIEF DESCRIPTION OF THE DRAWINGS

The accompanying drawings are included to provide a further understanding of the invention and are incorporated in and constitute part of the specification, illustrate several embodiments of the invention and, together with the description, serve to explain examples of the present invention. In the drawings:

FIG. 3 shows a cross-sectional view of a device used to implant the vessel seal of FIG. 1;

FIG. 4 shows a cross-sectional view of a sheath and a catheter of the device of FIG. 3 with a distal end thereof in place within the body lumen;

FIG. 5 shows a cross-sectional view of female reproductive organs with the catheter of FIG. 4 implanting the vessel seal of FIG. 1 therein; and FIG. 6 shows a second exemplary embodiment of the present invention in place within a body lumen.

DETAILED DESCRIPTION

Figure 1:
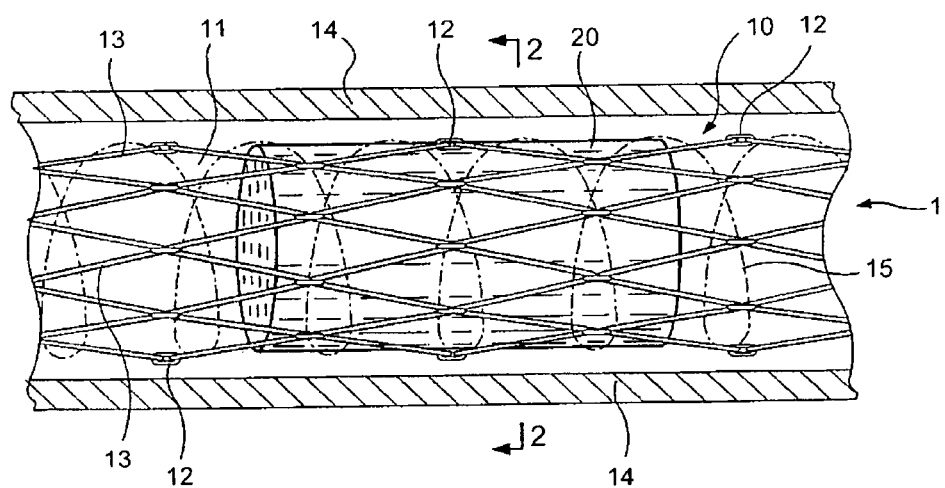
FIG. 1 shows a cut-away view of a body lumen with a reversible vessel seal apparatus according to a first exemplary embodiment of the present invention situated therein.
Figure 2:
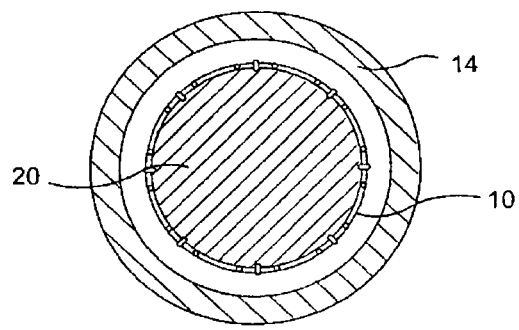
FIG. 2 shows a cross-sectional view of the body lumen of FIG. 1 taken along the line 2-2 of FIG. 1.

FIG. 1 shows a reversible vessel seal assembly 1 according to a first exemplary embodiment of the present invention. Those skilled in the art will recognize that, although the vessel seal according to the present invention is described herein in regard to contraceptive procedures, the vessel seal may be used in any procedure for which a vessel is to be sealed off indefinitely but which may need to be re-opened at a later date. As would be understood by those skilled in the art, the vessel 14 may be situated in either a human or an animal body where long term blockage is desired. The vessel 14 may be a vessel (e.g., fallopian tubes, vasa deferntia, etc.) that is connected to any organ (e.g., testes, ovaries, etc.) which needs to be blocked off without permanently altering or damaging the vessel and the surrounding tissue.

The vessel seal assembly 1 according to the present invention is preferably moveable between a compressed, insertion configuration and an expanded sealing configuration. This allows the vessel seal assembly 1 to be delivered/implanted in a vessel 14 in a compressed form thereby minimizing the trauma associated with the delivery. Once the vessel seal assembly 1 has been delivered to the vessel 14, it is released to expand to the block the vessel 14. The collapsibility of the vessel seal assembly 1 allows it to be delivered to the vessel 14 using minimally invasive means (e.g., via a catheter as described in further detail below), so that the outside walls of the vessel 14 remain intact. As described above, the vessel seal assembly 1 may remain in the vessel 14 indefinitely. However, if in the future the patient desires to reverse the effect of the blockage, the procedure is reversed by removing all or part of the vessel seal assembly 1 as described below.

As shown in FIG. 1, the vessel seal assembly 1 may include an intraluminal stent 10 and a removable vessel seal 20. The stent 10 may be comprised of a wire body 11 which may be constructed in any known manner as, for example, known configurations of self-expanding polymer or metal stents, such as the WALLSTENT® Endoprosthesis, the ULTRAFLEX® Precision Clonic Stent System and the POLYFLEX® Esophageal NG Stent System available from Boston Scientific Corporation of Natick, Mass.

A cross-section of the wire body 11 may, for example, be substantially round. Those skilled in the art will understand that other shapes (e.g., ellipsoidal, etc.) may also be utilized with the present invention depending upon the geometry of the lumen to be sealed. As would be understood by those of skill in the art, the wire body 11 may be composed of an elastic alloy which provides radial elasticity for the stent 10 and may more preferably comprise a nitinol alloy which has superior elasticity and fatigue resistance as well as shape memory properties. Alternatively, any biocompatible material of sufficient strength and elasticity may be used to form the wire body. Suitable materials include, for example, stainless steel, tantalum, titanium, or any one of a variety of plastics.

The stent 10 may also include a therapeutic coating over the wire body 11 to minimize trauma to the vessel 14 such as scarring or other damage that may be caused by the wires.

The wire body 11 may, for example, comprise a wire member 13, adjacent portions of which are interconnected with one another via coupling hoops 12 to form a mesh. More specifically, the stent may be composed of a wire member 13 which, when in the expanded configuration, extends along a zig-zag or sinusoidal path. An axis 15 about which this path oscillates (e.g., a zero axis of this sinusoidal or zig-zag path) extends along a helix with maximum amplitude portions of this path connected to points of maximum amplitude of the longitudinally adjacent windings of the wire member 13 via coupling hoops 12. Thus, the wire member 13 forms a cylinder with adjacent sections of the helix forming the cylinder supporting one another to increase an overall hoop strength of the stent structure. Those skilled in the art will recognize that this may minimize the risk of plaque herniation. The coupling hoops 12 may, for example, be ligatures of suture material with ends tied together to form a loop. This material may be polypropylene or any other biocompatible material of sufficient strength to indefinitely bind the adjacent helical portions the wire member 13 to one another despite stresses placed thereon in the environment into which the stent 10 is to be deployed. Although sutures are the preferred connecting means, other connecting means such as staples and rings made of metal or plastic may perform the same function.

The stent 10 is one of a plurality of support structures that may be used in the vessel seal assembly 1. There are a number of other embodiments that may be utilized as well. For instance, instead of having a mesh structure, as shown in FIG. 6, the stent 10 may have a coil structure 50 having the shape and form, when in the expanded configuration, of a substantially helical length of wire.

In each of the embodiments, a vessel seal 20 is located inside a central opening of the support structure which provides protection and structural support for the vessel seal 20. For example, in the case of the stent 10, the vessel seal 20 is securely attached to the stent 10 so that it will not detach therefrom even if the vessel seal 20 remains in place for the life of the patient. For instance, one or more loop members 12 may connect the vessel seal 20 to the wire body 11. In addition or alternatively, a locking mechanism (not shown) may be used to releaseably attach the vessel seal 20 to the stent 10 to facilitate later removal. The vessel seal 20 may also be pre-sutured to the stent 10 allowing for later removal by cutting these sutures.

As described above, the vessel seal 20 may have a substantially cylindrical shape or any other shape suitable to the geometry of the lumen to be sealed and is preferably composed of a compressible material or membrane that will expand with the stent 10 once the stent 10 has been delivered to the vessel 14 as discussed in detail below. The length of the vessel seal 20 may be selected based on the particular application and may extend outside of the support structure (e.g., stent 10). Alternatively, the vessel seal 20 may be shorter than the support structure, residing entirely therewithin, or may be coextensive therewith. The vessel seal 20 may be manufactured using any of a plurality of biocompatible, but not biodegradable materials (e.g., polytetrafluoroethylene (PTFE), dacron, etc.).

Certain materials and drugs may also be used to enhance the effectiveness of the vessel seal 20. For instance, metal particles known to have a contraceptive effect (e.g., copper) may be incorporated into the vessel seal 20. Furthermore, the vessel seal 20 may be coated with chemicals or drugs to create more effective blockage of the vessel 14. For instance, a vessel seal 20 to be implanted in the vasa deferntia, may be coated with spermicide to provide for additional contraception.

An exemplary method of implanting the vessel seal assembly 1 of the present invention includes the steps of: 1) forming a stent of a shape memory material (e.g., a Nitinol alloy) and impressing a memorized shape thereon corresponding to the expanded configuration; 2) coupling a vessel seal 20 thereto; 3) compressing the stent 10 and the vessel seal 20 into the insertion configuration; 4) introducing the stent 10 and the vessel seal 20 to a desired location within a body lumen to be sealed; and 5) releasing the stent 10 and the vessel seal 20 into the lumen so that the body heat of the patient induces the stent 10 to revert to the memorized shape of the expanded configuration. More specifically, as would be understood by those of skill in the art, the stent 10 may be formed of a Nitinol alloy selected to have a critical temperature slightly lower than the temperature of the environment in which the stent 10 is to be deployed (i.e., body temperature). Thus, the stent 10 may be manipulated into an insertion configuration (e.g., a minimum diameter shape such as a series of substantially straight wires) without regard to the stress placed thereon by this manipulation. The stent 10 may then be inserted into the body lumen via an introducing apparatus 16 and ejected therefrom at the desired location. Then, when the stent 10 is warmed above the critical temperature by the temperature in the lumen, the stent 10 will revert to its memorized shape (i.e., its expanded, deployed configuration). Alternatively, the stent 10 may be made of self-expanding material as with, for example, the wall stent, polyflex prostheses, ultraflex prostheses, etc., so that it expands to a memorized shape when deployed from the introducing apparatus 16.

The stent 10 and the vessel seal 20 may be introduced by known means introducer apparatus 16 may include a catheter 18 and a piston member 19 (e.g., a smaller diameter catheter) slidable within a central lumen of the catheter 18. The stent 10 and the vessel seal 20 are inserted into the central lumen of the catheter 18 in the compressed, insertion configuration and are advanced therethrough by the piston member 19 which is slid through the central lumen proximally of the stent 10 and the vessel seal 20, as shown in FIGS. 3 and 4. The stent 10 abuts the piston member 19 so that, if the catheter 18 is withdrawn proximally relative to the piston member 19, the stent 10 is exposed 10 to the body lumen.

Those skilled in the art will understand that the catheter 18 may be inserted to the desired location via natural passages of the patient's body after entering the body via a naturally occurring body orifice or may enter a body lumen through a small incision. For example, as shown in FIG. 5, in a tubal ligation procedure, the catheter 18 is inserted through the patient's vagina 32 in order to implant the vessel seal assembly 1 in one of the fallopian tubes 30. The catheter 18 is then withdrawn proximally relative to the piston member 19 until the stent 10 and the vessel seal 20 are exposed with the piston member 19 holding the stent 10 at the desired location within the body lumen. The final step involves removal of the catheter 19 to allow the stent 10 to expand. As the stent 10 expands, its diameter approaches the diameter of the vessel 14. Since the vessel seal 20 is made of a compressible material it conforms to the shape of the stent 10. In addition, due to the expansion of the stent 10, the vessel seal 20 also expands to fill the entire diameter of the vessel 14 and as a result seals the lumen thereof.

In an alternative exemplary embodiment of the present invention where the wire body 11 is made of a nitinol metal, a user may reduce a diameter of the stent 10 by first cooling it (e.g., by submerging it in ice water). This cooling places the nitinol in a martensitic phase and facilitates reduction of the diameter as stresses placed on the material will not impact the memorized shape to which the wire body 11 will revert when it is heated above the critical temperature. This allows for the insertion of the stent 10 into the central bore of a smaller diameter introducing apparatus 16. The vessel seal 20 may also be compressed at the same time as it is securely attached to the stent 10.

The introducer apparatus 16 and the sheath 18 restrain the stent 10 until it is deployed at the target location within the vessel 14. As described above, once the stent 10 has been positioned at the desired location, ambient environment warms the stent 10 to body temperature moving the nitinol into an austenitic phase which is the stable phase of this metal that corresponds to a fully opened or expanded configuration of the stent 10. As described above, the stent 10 and the vessel seal 20 are preferably selected to achieve a diameter substantially equal to an inner diameter of the body lumen at the target location to seal the vessel 14.

The expanded diameter of the stent 10 may also be selected to be slightly larger than the inner diameter of the body lumen so that the stent 10 urges the inner wall of the vessel 14 radially outward. Thus, the stent 10 provides a dilating force which supports the vessel 14 and the vessel seal 20. The structure of the stent 10 also provides flexibility which allows the stent 10 to follow the curvature of the vessel 14 in which it is placed.

The blockage of the vessel 14 via vessel seal assembly 1 can be reversed by removing the vessel seal 20 while leaving the stent 10 within the vessel 14 to provide support and protection thereto. The removal of the vessel seal 20 restores the fluid connection formerly provided by the vessel 14 and the functionalities to the organ to which the vessel 14 is connected. The vessel seal 20 may be removed in a variety of ways.

One exemplary technique for removing the vessel seal 20, is a laser removal procedure. In this laser removal procedure, laser energy is used to evaporate and remove the blockage (i.e., the vessel seal 20). In particular, the procedure involves placing a laser catheter in the vessel 14 and advancing it to the site of the vessel seal 20 as would be understood by those skilled in the art. The laser is powered, and laser energy is delivered to the vessel seal 20 to evaporate it. The laser catheter is then removed.

Another method for removal of the vessel seal 20 from the vessel 14 utilizes a rotational atherectomy procedure, as with the ROTOBLATOR® Burr Catheter. Rotational atherectomy utilizes a high speed rotational "burr" coated with microscopic diamond particles to drill through and break up the vessel seal 20. The "burr" rotates at a high speed (approximately 200,000 rpm), breaking up the vessel seal 20 into very small fragments (smaller than red blood cells) which pass harmlessly through the vessel 14.

Besides destroying the vessel seal 20 using any of the above-described techniques, the vessel seal 20 may be also coupled to the stent 10 by removable means (e.g., a suture). Such attachment means may facilitate removal by allowing the user to sever the vessel seal 20 from the stent 10 (e.g., by cutting the sutures) and removing the vessel seal 20 from the vessel 14.

The present invention allows for placement of a vessel seal assembly in a minimally invasive procedure reducing damage to the patient's body and the resulting discomfort. In addition, since the vessel 14 and surrounding blood vessels are not damaged during this procedure, the flow of vital materials to the connected organ is not interrupted and the organ will be better able to maintain its functionality.

It will be apparent to those skilled in the art that various modifications and variations can be made in the structure and the methodology of the present invention, without departing from the spirit or scope of the invention. Thus, it is intended that the present invention cover the modifications and variations of this invention provided they come within the scope of the appended claims and their equivalents.

What is claimed is:

1. A reversible vessel seal for reversibly sealing a body lumen comprising:
a support structure including a wire, the support structure moveable between an insertion configuration and a deployed configuration, wherein a diameter of the support structure is greater in the deployed configuration than in the insertion configuration, a diameter of the support structure in the deployed configuration substantially corresponding to an inner diameter of a target portion of the body lumen at which the support structure is to be deployed; and
a compressible vessel seal made of a compressible material that conforms to the shape of the support structure and is coupled to the support structure, wherein when the support structure is expanded to the deployed configuration in a body lumen, the vessel seal expands within a central lumen of the support structure to occlude the entire diameter of the body lumen, wherein the vessel seal is releasably attached to the support structure, and wherein the compressible vessel seal comprises a biocompatible, non-biodegradable material.

2. A reversible vessel seal according to claim 1, wherein the support structure is a stent.

3. A reversible vessel seal according to claim 2, wherein the stent is comprised of a shape memory material.

4. A reversible vessel seal according to claim 3, wherein the shape memory material is nitinol.

5. A reversible vessel seal according to claim 3, wherein, in the deployed configuration, the stent reverts to a memorized shape.

6. A reversible vessel seal according to claim 5, wherein the stent reverts to the memorized shape when it is warmed above a critical temperature.

7. A reversible vessel seal according to claim 1, wherein the vessel seal is releasably attached to the support structure using sutures.

8. A reversible vessel seal according to claim 1, wherein the vessel seal is releasably attached to the support structure using a locking mechanism.

9. A reversible vessel seal according to claim 1, wherein each of the plurality of points of maximum amplitude of curvature are joined to the corresponding points of maximum curvature of the adjacent coil by loops of suture.

10. A reversible vessel seal according to claim 1, wherein the support structure is coupled to the vessel seal by suture.

11. A reversible vessel seal according to claim 1, wherein said biocompatible, non-biodegradable material is solid biocompatible, non-biodegradable material.

12. A method of controlling flow through a body lumen, comprising the steps of:
   inserting into a target portion of a body lumen a vessel seal assembly in an insertion configuration, the vessel seal assembly including a support structure including a wire and a compressible vessel seal made of a compressible material that conforms to the shape of the support structure and is coupled thereto; and
   moving the support structure to a deployed configuration in which the vessel seal expands within a central lumen of the support structure to occlude the entire diameter of the body lumen, wherein a diameter of the support structure is greater in the deployed configuration than in the insertion configuration and a diameter of the support structure in the deployed configuration substantially corresponds to an inner diameter of the target portion of the body lumen, wherein the vessel seal is releasably attached to the support structure, and wherein the compressible vessel seal comprises a biocompatible, non-biodegradable material.

13. A method according to claim 12, further comprising the step of restoring flow through the body lumen by removing the vessel seal from the support structure.

14. A method according to claim 13, wherein the vessel seal is coupled to the support structure by sutures and wherein the vessel seal is removed from the support structure by cutting the sutures.

15. A reversible vessel seal according to claim 12, wherein said biocompatible, non-biodegradable material is solid biocompatible, non-biodegradable material.

* * * * *